(12) United States Patent
Mimitsuka et al.

(10) Patent No.: US 10,370,633 B2
(45) Date of Patent: Aug. 6, 2019

(54) METHOD OF OPERATING CONTINUOUS STERILIZING APPARATUS, CONTINUOUS STERILIZING APPARATUS, FERMENTING SYSTEM, AND CONTINUOUS FERMENTING SYSTEM

(71) Applicant: Toray Industries, Inc., Tokyo (JP)

(72) Inventors: Takashi Mimitsuka, Kamakura (JP); Hiroshi Hayakawa, Nagoya (JP); Ken Morita, Nagoya (JP); Yuki Yamamoto, Mishima (JP); Kenichi Otsuka, Otsu (JP)

(73) Assignee: Toray Industries, Inc., Tokyo (JP)

( * ) Notice: Subject to any disclaimer, the term of this patent is extended or adjusted under 35 U.S.C. 154(b) by 481 days.

(21) Appl. No.: 14/899,624

(22) PCT Filed: Jun. 23, 2014

(86) PCT No.: PCT/JP2014/066516
§ 371 (c)(1),
(2) Date: Dec. 18, 2015

(87) PCT Pub. No.: WO2014/208485
PCT Pub. Date: Dec. 31, 2014

(65) Prior Publication Data
US 2016/0145559 A1  May 26, 2016

(30) Foreign Application Priority Data
Jun. 24, 2013  (JP) ................................ 2013-131894

(51) Int. Cl.
*C12M 1/12* (2006.01)
*A23L 3/22* (2006.01)
(Continued)

(52) U.S. Cl.
CPC .............. *C12M 37/00* (2013.01); *A23L 3/22* (2013.01); *A61L 2/07* (2013.01); *C12M 33/14* (2013.01);
(Continued)

(58) Field of Classification Search
CPC ...... C12M 37/00; C12M 45/00; C12M 45/20; C12M 41/12; C12M 33/14; C12M 47/16;
(Continued)

(56) References Cited

U.S. PATENT DOCUMENTS 2,338,228 A  1/1944 Boeckeler et al.
4,597,945 A  7/1986 Sugisawa et al.
(Continued)

FOREIGN PATENT DOCUMENTS

EP  1 616 938  1/2006
EP  2 279 674  2/2011
(Continued)

OTHER PUBLICATIONS

English translation of JP 2000-262594 (Year: 2000).*
(Continued)

*Primary Examiner* — Regina M Yoo
(74) *Attorney, Agent, or Firm* — DLA Piper LLP (US)

(57) ABSTRACT

A continuous sterilizing apparatus circulates, through members constituting a flow channel, a sterilizing medium that sterilizes the members to sterilize the members, circulates a sterilizing liquid subjected to sterilization treatment through pipes, performs a series of pieces of treatment including heating treatment, holding treatment, and cooling treatment on the sterilizing liquid, controls a flow rate, a temperature, and a pressure to be preset conditions, and switches a liquid to be circulated through the flow channel from the sterilizing liquid to a liquid to be sterilized.

9 Claims, 10 Drawing Sheets

(51) Int. Cl.
*A61L 2/07* (2006.01)
*C12M 1/26* (2006.01)
*C12M 1/34* (2006.01)
*C12M 1/00* (2006.01)

(52) U.S. Cl.
CPC ............ *C12M 41/00* (2013.01); *C12M 41/12* (2013.01); *C12M 41/40* (2013.01); *C12M 45/00* (2013.01); *C12M 45/20* (2013.01); *C12M 47/16* (2013.01); *A23V 2002/00* (2013.01)

(58) Field of Classification Search
CPC ......... C12M 41/00; C12M 41/40; A61L 2/07; A23L 3/22
See application file for complete search history.

(56) References Cited

U.S. PATENT DOCUMENTS

| | | | | |
|---|---|---|---|---|
| 6,579,494 | B1* | 6/2003 | Chevallet | A61L 2/0023 |
| | | | | 210/143 |
| 8,137,542 | B2* | 3/2012 | Abe | B01D 61/18 |
| | | | | 210/138 |
| 8,381,494 | B2* | 2/2013 | Krakers | B65B 55/04 |
| | | | | 53/167 |
| 8,663,556 | B2 | 3/2014 | Kariyama et al. | |
| 2008/0160149 | A1* | 7/2008 | Nasrallah | A23L 2/46 |
| | | | | 426/521 |
| 2009/0166276 | A1 | 7/2009 | Abe et al. | |

FOREIGN PATENT DOCUMENTS

| | | | |
|---|---|---|---|
| JP | 60-182950 | | 9/1985 |
| JP | S62-208268 | A | 9/1987 |
| JP | 01-148180 | A | 6/1989 |
| JP | H6-253816 | A | 9/1994 |
| JP | 2904779 | | 6/1999 |
| JP | 2000-262594 | A | 9/2000 |
| JP | 2003-289838 | A | 10/2003 |
| JP | 2009-154135 | A | 7/2009 |
| JP | 2011-078493 | A | 4/2011 |
| JP | 2012-161288 | A | 8/2012 |
| WO | WO-9800175 A1 * | 1/1998 | ............ A23C 3/033 |
| WO | 2009/145198 A1 | 10/2011 | |
| ZA | 9705712 | 12/1998 | |

OTHER PUBLICATIONS

Supplementary European Search Report dated Jun. 1, 2017, of corresponding European Application No. 14817532.6.

Notification of Reasons for Refusal dated Aug. 28, 2018, of counterpart Japanese Application No. 2014-531005, along with an English translation.

* cited by examiner

METHOD OF OPERATING CONTINUOUS STERILIZING APPARATUS, CONTINUOUS STERILIZING APPARATUS, FERMENTING SYSTEM, AND CONTINUOUS FERMENTING SYSTEM

TECHNICAL FIELD

This disclosure relates to a method of operating a continuous sterilizing apparatus, a continuous sterilizing apparatus, a fermenting system, and a continuous fermenting system for sterilizing liquid culture media, food products, pharmaceuticals, or the like into a microbiologically safe state.

BACKGROUND

Methods of culturing microorganisms or cultured cells and continuously collecting products are known. Specifically, a method of continuous fermentation is developed that separates a product from a microorganism or the like using a filtration membrane and returns the microorganism or the like contained in an unfiltrated liquid to a culture liquid again.

In the method of continuous fermentation, a sterilized culture medium is continuously supplied to culture a microorganism or cultured cell continuously. To continuously supply the sterilized culture medium, the method of continuous fermentation uses a continuous sterilizing apparatus that can continuously sterilize the culture medium. The continuous sterilizing apparatus can sterilize the culture medium by short-time heating treatment.

To industrially produce fermented products at low prices, in general, a large volume of products are desired to be produced at a time. In this case, a fermenter of a fermenting apparatus for use in continuous fermentation treatment has a scale of several hundreds of tons. When sterilization treatment is performed on a culture medium housed in a fermenter of this scale, it requires long time to heat the culture medium at the center of the fermenter to a temperature appropriate for sterilization, and the culture medium may deteriorate through long hours of heating. Given these circumstances, batch sterilization that performs sterilization practically for each fermenter is not performed as culture medium sterilization treatment. For this reason, a continuous sterilizing apparatus that can perform high-temperature, short-time sterilization and can minimize deterioration of a culture medium through heating is suitably used in culture medium sterilization treatment.

The continuous sterilizing apparatus includes a heating unit that heats a liquid to be sterilized, a holding unit that holds the temperature of the heated liquid to be sterilized for a set time to perform sterilization, and a cooling unit that can cool the sterilized liquid to be sterilized nearly to room temperature (refer to Japanese Laid-open Patent Publication No. 2000-262594, for example).

The continuous sterilizing apparatus includes, as a form of heating the liquid to be sterilized, a multi-pipe type, a plate type, and a steam injector type. The steam injector type is a type of directly introducing steam into the liquid to be sterilized, can instantaneously increase the temperature of the liquid to be sterilized, and can simultaneously sterilize the inside of the continuous sterilizing apparatus (refer to Japanese Laid-open Patent Publication No. 01-148180, for example). However, a boiler compound (an anticorrosive) usually mixes with steam used in industrial processes, and the boiler compound mixing with a culture medium may affect fermenting performance. For this reason, in fermenting processes such as a method of continuous fermentation, the multi-pipe type or plate type is used. Although the multi-pipe type and plate type can perform continuous sterilization treatment without using the boiler compound, heating treatment enough for instantaneously increasing the temperature of the liquid to be sterilized cannot be performed, unlike the steam injector type.

FIG. 10 is a schematic diagram illustrating an example of a rough configuration of a conventional multi-pipe type continuous sterilizing apparatus. The continuous sterilizing apparatus 100 illustrated in FIG. 10 includes a pressure feed pump 101 that pressure feeds a culture medium, a food product, or a pharmaceutical (hereinafter, referred to as a liquid to be sterilized) to be pressure-fed and a sterilizing liquid, a heating unit 102 that heats the liquid to be sterilized or the sterilizing liquid sent by the pressure feed pump 101, a holding unit 103 that holds the liquid to be sterilized or the sterilizing liquid heated by the heating unit 102 at a certain temperature for a certain time, a cooling unit 104 that cools the liquid to be sterilized or the sterilizing liquid held by the holding unit 103 and for which heating sterilization has been completed, and a cooling unit 105 provided at the rear of the cooling unit 104 and cools the sterilizing liquid, which are connected to each other with pipes to form a flow channel. Operation of the continuous sterilizing apparatus 100 is controlled by a controller (not illustrated).

In the continuous sterilizing apparatus 100, the pressure feed pump 101, the heating unit 102, the holding unit 103, and the cooling unit 104 are connected in order with a pipe 106 to form a first flow channel as a flow channel. In addition, in the continuous sterilizing apparatus 100, a second flow channel is formed by connecting an upstream side end and a downstream side end of the pipe 106 and both ends of a pipe 107. The cooling unit 105 is provided in the second flow channel.

The pipe 106 includes a valve 111 provided at the front of the pressure feed pump 101 and valves 112 and 113 provided at the rear of the cooling unit 104. The valve 112 is provided at the front (upstream side) of a connecting part between the pipe 106 and the pipe 107, whereas the valve 113 is provided at the rear (downstream side) of the connecting part between the pipe 106 and the pipe 107. The pipe 107 includes valves 114 and 115 provided near the respective connecting parts with the pipe 106. The valve 114 is provided at a connecting part with the downstream side of the first flow channel (the pipe 106) in the pipe 107. The valve 115 is provided at a connecting part with the upstream side of the first flow channel in the pipe 107.

The heating unit 102 circulates steam through the inside of a pipe 102a provided along the pipe 106, thereby heating the pipe 106. The cooling units 104 and 105 circulate cooling water through the inside of pipes 104a and 105a provided along the pipes 106 and 107, respectively, thereby cooling the pipes 106 and 107, respectively.

The continuous sterilizing apparatus 100 circulates the sterilizing liquid through the inside of the pipes 106 and 107 to perform sterilization treatment on the inside of the pipes as pretreatment of continuous sterilization treatment before circulating the actual liquid to be sterilized. Specifically, with the valves 112, 114, and 115 open and with the valves 111 and 113 closed, the sterilizing liquid is circulated through the inside of the pipes 106 and 107 by the pressure feed pump 101, thereby sterilizing the inside of the pipes 106 and 107. In that situation, the sterilizing liquid circulates through the pipes heated up to about 135° C. by the heating unit 102 and is cooled to about 50° C. by the cooling unit 105. The continuous sterilizing apparatus 100 adjusts the operation of the pressure feed pump 101 and an open state of the valve 112 by the controller, thereby controlling a flow rate and pressure within the pipes. During the sterilization treatment, the cooling unit 104 stops its cooling operation. With this operation, the sterilizing liquid circulates through the pipe 106 heated up to about 135° C. to sterilize the inside of the pipe, is cooled by the cooling unit 105, and again flows into the heating unit 102.

After the sterilization treatment with the sterilizing liquid, the cooling unit 104 is operated to stabilize a cooling temperature inside the pipe 106 in the cooling unit 104. Control to open the valve 113 and to close the valves 114 and 115 is then performed, the valve 111 is opened to switch from the sterilizing liquid to the liquid to be sterilized, and the continuous sterilization treatment on the liquid to be sterilized is performed.

In the conventional continuous sterilizing apparatus 100, the cooling unit 105 is provided in the second flow channel used for the pretreatment, in addition to the first flow channel as the original sterilizing channel, and the apparatus is disadvantageously large in scale.

It could therefore be helpful to provide a method of operating a continuous sterilizing apparatus, a continuous sterilizing apparatus, a fermenting system, and a continuous fermenting system that can surely perform sterilization treatment on the inside of a flow channel and achieve downsizing of the apparatus.

SUMMARY

We thus provide:

A method of operating a continuous sterilizing apparatus includes continuously performing a series of pieces of treatment including heating treatment, holding treatment, and cooling treatment on a flow channel through which a liquid to be sterilized circulates to perform sterilization on the liquid to be sterilized, and includes: circulating a sterilizing medium that sterilizes members forming the flow channel through the flow channel to sterilize the member; circulating a sterilizing liquid subjected to sterilization treatment through the members, performing the series of pieces of treatment on the sterilizing liquid, and measuring a flow rate, a temperature, and a pressure of the sterilizing liquid subjected to the series of pieces of treatment; comparing the flow rate, the temperature, and the pressure measured with respect to the sterilizing liquid subjected to the series of pieces of treatment with a flow, a temperature, and a pressure as preset conditions and determining whether the measured flow, temperature, and pressure satisfy the conditions; and switching, when it is determined that the conditions are satisfied at the determining, the liquid to be circulated through the members from the sterilizing liquid to the liquid to be sterilized.

The above-described method, wherein the sterilizing medium is steam.

The above-described method, wherein the series of pieces of treatment comprise heat exchange treatment between liquids before and after being subjected to the heating treatment and the holding treatment.

The above-described method, wherein the liquid to be sterilized is a culture medium as a fermentation raw material.

The above-described method, wherein the sterilizing liquid and the liquid to be sterilized are successively supplied to a fermenting apparatus that performs fermentation treatment.

A continuous sterilizing apparatus sterilizes a liquid to be sterilized and includes: a first circulating unit including: a heating unit configured to heat the liquid to be sterilized; a holding unit configured to hold the liquid to be sterilized heated by the heating unit at a certain temperature for a certain time; and a cooling unit configured to cool the liquid to be sterilized held by the holding unit and for which heating sterilization has been completed, and the first circulating unit is configured to circulate at least the liquid to be sterilized; a second circulating unit configured to introduce a sterilizing medium that sterilizes members forming a flow channel from one end, and connected to the first circulating unit at another end; a third circulating unit configured to introduce a sterilizing liquid subjected to sterilization treatment from one end and connected to the first circulating unit at another end; a measuring unit configured to measure a flow rate, a temperature, and a pressure of a liquid circulating through the first circulating unit; a storage unit configured to store a flow rate, a temperature, and a pressure related to sterilization treatment on the liquid to be sterilized as condition information; and a controller configured to control entire operation of the continuous sterilizing apparatus, the controller being configured to: control the second and the third circulating units to circulate the sterilizing medium through the first circulating unit to sterilize the first circulating unit and then circulate the sterilizing liquid through the first circulating unit; perform a series of treatment by the heating unit, the holding unit, and the cooling unit on the sterilizing liquid and cause the measuring unit to measure a flow rate, a temperature, and a pressure of the sterilizing liquid subjected to the series of pieces of treatment, and compare the flow rate, the temperature, and the pressure measured by the measuring unit with the condition information stored in the storage unit, determine whether the measured flow rate, temperature, and pressure satisfy conditions corresponding to the condition information, and control the first and the third circulating units, when it is determined that the conditions are satisfied, to switch the liquid to be circulated through the first circulating unit from the sterilizing liquid to the liquid to be sterilized.

The above-described continuous sterilizing apparatus, wherein the sterilizing medium is steam, and the continuous sterilizing apparatus further includes a fourth circulating unit connected to the first circulating unit and configured to discharge drain generated by the steam.

The above-described continuous sterilizing apparatus further includes a heat exchange unit configured to cause heat exchange between respective liquids that circulate through an upstream side of the heating unit and a downstream side of the hold unit.

The above-described continuous sterilizing apparatus, wherein at least one of the heating unit, the cooling unit, and the heat exchange unit is a plate type heat exchanger.

A fermenting system includes: a raw material hold unit configured to hold a raw material such as a culture medium, a food product, and a pharmaceutical; the above-described continuous sterilizing apparatus continuously sterilizing the raw material supplied from the raw material hold unit as the liquid to be sterilized; and a fermenter configured to perform fermentation treatment using the raw material subjected to sterilization treatment by the continuous sterilizing apparatus.

The above-described fermenting system, wherein the flow rate is determined in accordance with a measurement result by the measuring unit, a weight change of the raw material holding unit, and/or a weight change of the fermenter.

The above-described fermenting system, wherein the sterilizing liquid is introduced via a pipe diverted from a pipe that introduces the sterilizing liquid to the fermenter.

A continuous fermenting system includes: the above-described fermenting system; and a filtration unit configured to filtrate a fermented liquid generated in the fermenter.

In the continuous fermenting system, the raw material hold unit comprises a plurality of raw material holding units.

We can thus perform sterilization treatment on the inside of flow channels and can achieve downsizing of the apparatus.

Figure 1:
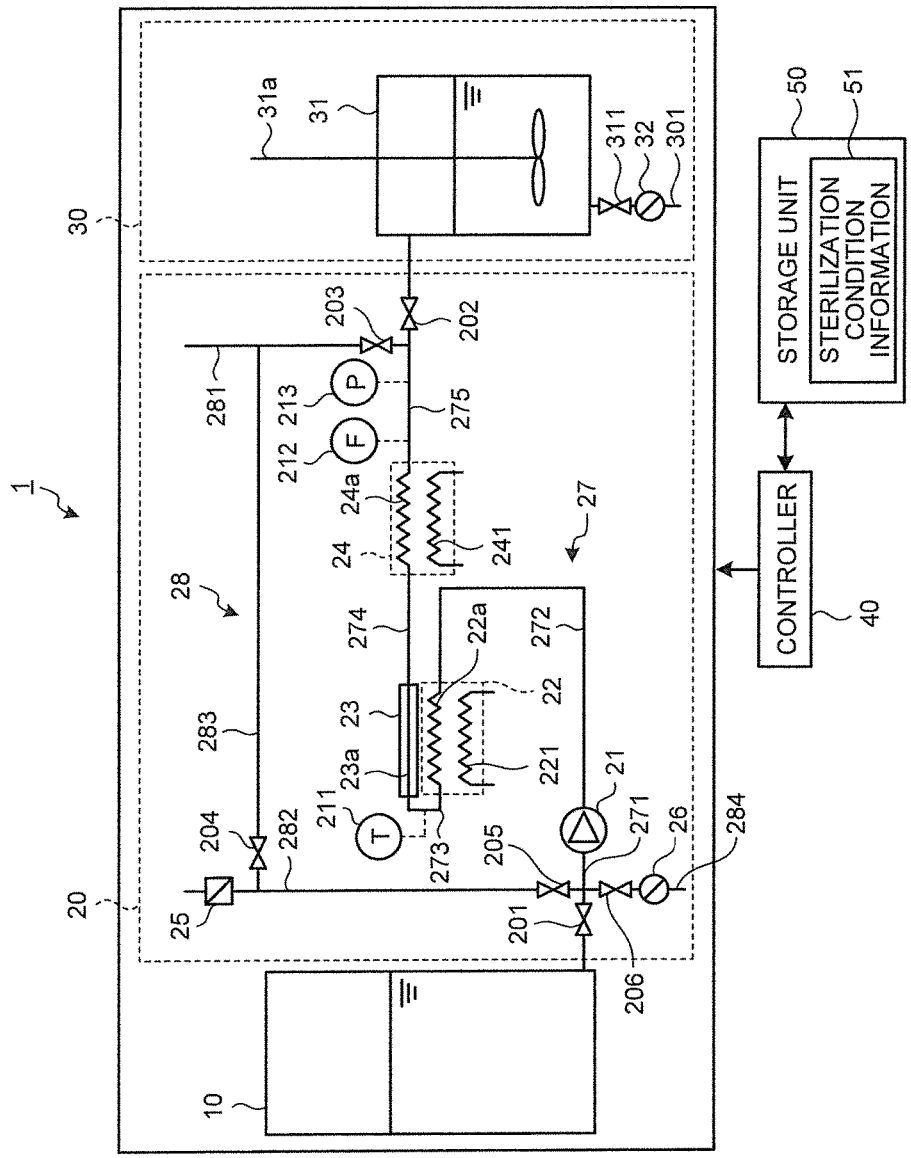
FIG. 1 is a schematic diagram illustrating a rough configuration of a fermenting system according to a first example.

REFERENCE SIGNS LIST 1, 1a Fermenting system
2, 2a Continuous fermenting system
10 Raw material holding unit
20, 20a, 100 Continuous sterilizing apparatus
21, 33, 101 Pressure feed pump
22, 102 Heating unit
22a, 23a, 24a, 221, 241, 291, 292 Pipe
23, 103 Holding unit
24, 104 Cooling unit
25 Sterilizing filter
26, 32 Steam trap
27, 27a First flow channel
28 Second flow channel
29 Heat exchange unit
29a First heat exchange unit
29b Second heat exchange unit
30, 30a Fermenting apparatus
31 Fermenter
31a Stirring unit
34 Separation membrane module
40, 40a Controller
50 Storage unit
51 Sterilization condition information
201 First valve
202 Second valve
203 Third valve
204 Fourth valve
205 Fifth valve
206 Sixth valve
211 Thermometer
212 Flow meter
213 Pressure gauge
271, 281, 301 First pipe
272, 282, 302 Second pipe
273, 283, 303 Third pipe
274, 284, 304 Fourth pipe
275 Fifth pipe
276 Sixth pipe
277 Seventh pipe
278 Eighth pipe
279 Ninth pipe
311 Valve
341 Porous film

DETAILED DESCRIPTION

The following describes detailed examples. The following examples do not limit this disclosure.

First Example

FIG. 1 is a schematic diagram illustrating a rough configuration of a fermenting system according to a first example. This fermenting system 1 houses a microorganism for culture or a cultured cell and continuously supplies a sterilized culture medium to a fermenter that generates a fermented liquid by fermentation.

The fermenting system 1 illustrated in FIG. 1 includes a raw material holding unit 10 that holds a raw material such as a culture medium, a food product, and a pharmaceutical, a continuous sterilizing apparatus 20 that continuously sterilizes the raw material supplied from the raw material holding unit 10, a fermenting apparatus 30 that performs fermentation treatment using the raw material subjected to the sterilization treatment by the continuous sterilizing apparatus 20, a controller 40 that includes a central processing unit (CPU) and controls the entire operation of the fermenting system 1, and a storage unit 50 that stores therein various kinds of programs of operating the fermenting system 1 and information containing various kinds of parameters required for the operation of the fermenting system 1.

The continuous sterilizing apparatus 20 includes a pressure feed pump 21 that pressure feeds a culture medium, a food product, or a pharmaceutical (hereinafter, referred to as a liquid to be sterilized) to be pressure-fed or a sterilizing liquid subjected to sterilization treatment, a heating unit 22 that heats the liquid to be sterilized or the sterilizing liquid fed by the pressure feed pump 21, a holding unit 23 that holds the liquid to be sterilized or the sterilizing liquid heated by the heating unit 22 at a certain temperature for a certain time, a cooling unit 24 that cools the liquid to be sterilized or the sterilizing liquid held by the holding unit 23 and for which heating sterilization has been completed, a sterilizing filter 25 that performs sterilization treatment, and a steam trap 26 that discharges only drain within a steam atmosphere. The controller 40 controls the operation of the continuous sterilizing apparatus 20. For example, sterilized water adjusted to have a viscosity or the like similar to that of the actual liquid to be sterilized is used as the sterilizing liquid. An aqueous solution subjected to sterilization treatment may be used as the sterilizing liquid so long as it is adjusted to have a viscosity or the like similar to that of the actual liquid to be sterilized. The sterilizing liquid subjected to sterilization treatment may be, for example, condensed water of pure steam (steam that contains no boiler compound) or water sterilized with a sterilizing filter. The sterilizing liquid is preferably water sterilized with a sterilizing filter.

In the continuous sterilizing apparatus 20, the pressure feed pump 21, the heating unit 22, the holding unit 23, and the cooling unit 24 are connected with pipes in order, and these members form a first flow channel 27 (a first circulating unit) as a flow channel. The continuous sterilizing apparatus 20 forms a second flow channel 28 respective both ends of which connect to an upstream side and a downstream side of the first flow channel 27. In the first flow channel 27, a side connected to the raw material holding unit 10 is defined as the upstream side, whereas the side connected to the fermenting apparatus 30 is defined as the downstream side.

The first flow channel 27 includes a first pipe 271 one end of which connects to the raw material holding unit 10 and the other end of which connects to the pressure feed pump 21, a second pipe 272 that connects between the pressure feed pump 21 and the heating unit 22, a third pipe 273 that connects between the heating unit 22 and the holding unit 23, a fourth pipe 274 that connects between the holding unit 23 and the cooling unit 24, and a fifth pipe 275 one end of which connects to the cooling unit 24 and the other end of which connects to the fermenting apparatus 30.

The first pipe 271 includes a first valve 201 that restricts the circulation of a gas or liquid within the pipe through its opening and closing. The fifth pipe 275 includes a second valve 202 that restricts the circulation of a gas or liquid within the pipe through its opening and closing. The first valve 201 automatically opens and closes under the control of the controller 40. The second valve 202 automatically adjusts its degree of opening under the control of the controller 40.

The continuous sterilizing apparatus 20 includes a thermometer 211 provided in the third pipe 273 and measures the temperature of a liquid circulating through the third pipe 273, a flow meter 212 provided in the fifth pipe 275 and measures the flow rate of a liquid circulating through the fifth pipe 275, and a pressure gauge 213 provided in the fifth pipe 275 and measures the pressure within the fifth pipe 275.

The second flow channel 28 includes a first pipe 281 one end of which can introduce steam or a liquid and the other end of which connects to a part of the fifth pipe 275 that is upstream side of the second valve 202, a second pipe 282 one end of which can introduce steam and the other end of which connects to between the first valve 201 of the first pipe 271 and the pressure feed pump 21, a third pipe 283 one end of which connects to the first pipe 281 and the other end of which connects to the second pipe 282, and a fourth pipe 284 one end of which connects to between the first valve 201 of the first pipe 271 and the pressure feed pump 21. The above pipes are connected with respective connectors (not illustrated).

The first pipe 281 is preferably introduced from the highest position of the continuous sterilizing apparatus 20. Introducing steam from an upper part (a high position) of the continuous sterilizing apparatus 20 is common technical knowledge, and when the fifth pipe 275 is higher than the first pipe 271, for example, the other end of the first pipe 281 connects to the upstream side of the second valve 202 of the fifth pipe 275.

The sterilizing filter 25 is provided in the second pipe 282 at the upstream side (a liquid introducing side) of a connecting part with the third pipe 283. With this configuration, a liquid introduced from the one end of the second pipe 282 is sterilized by the sterilizing filter 25.

The steam trap 26 is provided in the fourth pipe 284. The fourth pipe 284 is preferably provided at the bottom of the continuous sterilizing apparatus 20 for drain (condensation) discharge caused by steam. When the continuous sterilizing apparatus 20 includes a plurality of bottoms, for example, the fourth pipe 284 and the steam trap 26 are provided at each bottom.

The first pipe 281 includes a third valve 203 provided near a connecting part with the fifth pipe 275 and restricts the circulation of a gas or liquid within the pipe through its opening and closing.

The third pipe 283 includes a fourth valve 204 that restricts the circulation of a gas or liquid within the pipe through its opening and closing.

The second pipe 282 includes a fifth valve 205 provided in between a connecting part with the first pipe 271 and a connecting part with the third pipe 283 and restricts the circulation of a gas or liquid within the pipe through its opening and closing.

The fourth pipe 284 includes a sixth valve 206 provided in between a connecting part with the first pipe 271 and the steam trap 26 and restricts the circulation of a gas or liquid within the pipe through its opening and closing.

The third valve 203 through the sixth valve 206 are operated to open and close automatically under the control of the controller 40.

The heating unit 22 includes a pipe 22a one end of which connects to the second pipe 272 and the other of which connects to the third pipe 273 and a pipe 221 that is provided near or in outer surface contact with the pipe 22a. The heating unit 22 heats the pipe 22a by circulating steam through the inside of the pipe 221.

The holding unit 23 includes a pipe 23a one end of which connects to the third pipe 273 and the other end of which connects to the fourth pipe 274 and maintains the pipe 23a at a certain temperature. The length of the pipe 23a is preferably determined in accordance with a holding time and a flow rate.

The cooling unit 24 includes a pipe 24a one end of which connects to the fourth pipe 274 and the other end of which connects to the fifth pipe 275 and a pipe 241 provided near or in outer surface contact with the pipe 24a. The cooling unit 24 cools the pipe 24a by circulating cooling water through the inside of the pipe 241.

A plate type heat exchanger that performs heat exchange via a heat exchanger wall is preferably used for the heating unit 22 and the cooling unit 24. The heating unit 22 may be, for example, one that provides a heat exchanger wall in between the pipe 22a and the pipe 221 to facilitate heat exchange or one that divides one pipe with a heat exchanger wall, circulates a liquid to be sterilized or the like through one divided area, and circulates a heating medium such as steam and hot water through the other area.

The sterilizing filter 25 has a function to remove a microorganism within a liquid.

The steam trap 26 has a function to automatically discharge an accumulated drain based on information on a water level accumulated in itself, internal temperature, or the like.

The fermenting apparatus 30 includes a fermenter 31 coupled to the continuous sterilizing apparatus 20 and houses and ferments a culture medium, a food product, or a pharmaceutical sterilized by the continuous sterilizing apparatus 20 and a microorganism, a cultured cell, or the like and a steam trap 32 that discharges only drain within a steam atmosphere.

The fermenting apparatus 30 includes a first pipe 301 one end of which connects to the fermenter 31. The first pipe 301 includes the steam trap 32. The first pipe 301 includes a valve 311 provided in between a connecting part with the fermenter 31 and the steam trap 32 and restricts the circulation of a liquid within the pipe through its opening and closing operation under the controller 40.

The fermenter 31 includes a stirring unit 31a. The stirring unit 31a includes a stirring vane at the tip of a rod-shaped member. The fermenter 31 stirs the housed liquid through the rotation of the stirring vane of the stirring unit 31a. The fermenter 31 can attach sensors that measure temperature and pH controlled in normal fermentation. The fermenter 31 has functions that should be naturally provided as a fermenter such as capability of permeating a gas.

The storage unit 50 stores therein sterilization condition information 51 related to sterilization treatment on the liquid to be sterilized. The sterilization condition information 51 contains information on a heating temperature in the heating unit 22, a holding time in the holding unit 23, a cooling temperature in the cooling unit 24, a flow rate in the first flow channel 27, and intra-pipe pressure in the first flow channel 27. The storage unit 50 is implemented using a semiconductor memory such as a flash memory and a dynamic random access memory (DRAM).

In the fermenting system 1, the raw material supplied from the raw material holding unit 10 is fed to the heating unit 22 by the pressure feed pump 21 via the first pipe 271. Subsequently, the raw material heated (heated up to 135° C., for example) by the heating unit 22 is fed to the holding unit 23 and is held for a certain time (1 minute, for example) at a certain temperature (135° C., for example). With this operation, heating sterilization treatment is performed on the raw material. The raw material subjected to the heating sterilization treatment is sent to the cooling unit 24 and cooled (cooled to about 32° C., for example). The raw material cooled by the cooling unit 24 is fed to the fermenter 31 via the fifth pipe 275. In the fermenter 31, fermentation treatment is performed on the raw material fed from the continuous sterilizing apparatus 20 and the microorganism or cultured cell. By performing the series of pieces of treatment, the raw material sterilized by the continuous sterilizing apparatus 20 is continuously supplied to the fermenter 31, in which the fermentation treatment is performed, and a fermented liquid can be collected. In the series of pieces of treatment, the controller 40 performs control to open only the first valve 201 and the second valve 202 and close the third valve 203 through the sixth valve 206 and the valve 311.

The following describes sterilization treatment (a method of operating the continuous sterilizing apparatus 20) by the continuous sterilizing apparatus 20 of the fermenting system 1. The continuous sterilizing apparatus 20 sterilizes the continuous sterilizing apparatus 20 as pretreatment of the sterilization treatment on the liquid to be sterilized such as a culture medium, a food product, and a pharmaceutical before sterilizing the actual liquid to be sterilized. After sterilizing the continuous sterilizing apparatus 20, sterilized water is circulated through the first flow channel 27, thereby stabilizing a sterilization temperature, a pressure, a flow rate, or the like of the continuous sterilizing apparatus 20.

Figure 2:
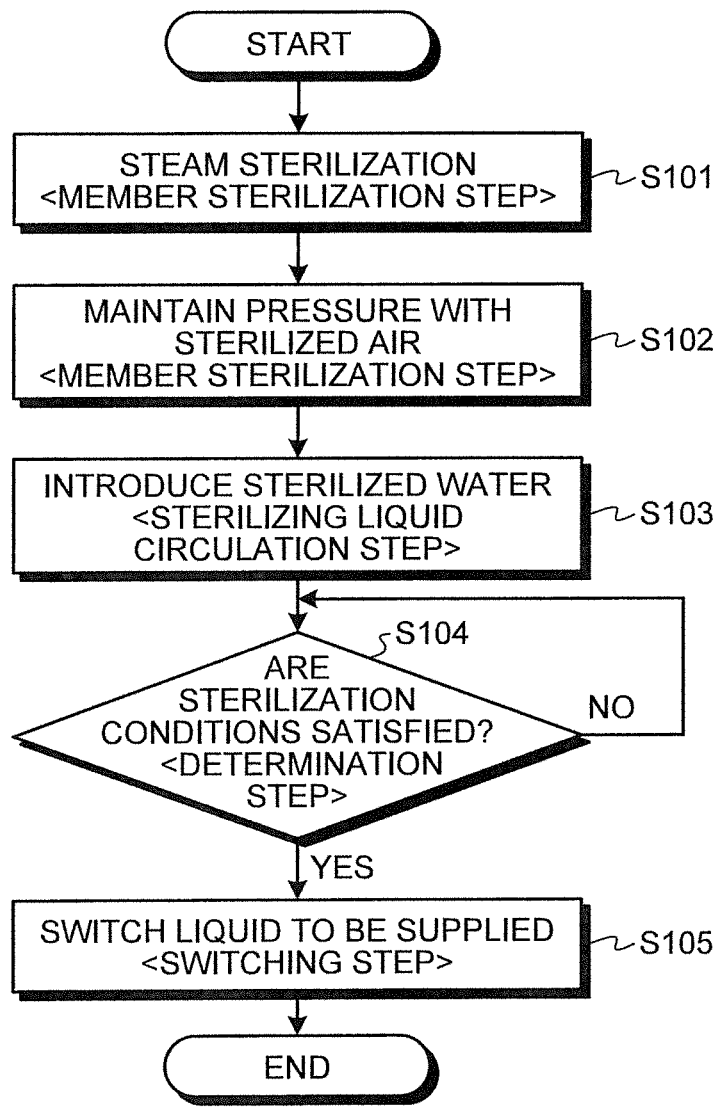
FIG. 2 is a flowchart illustrating pretreatment in the fermenting system according to the first example.
Figure 3:
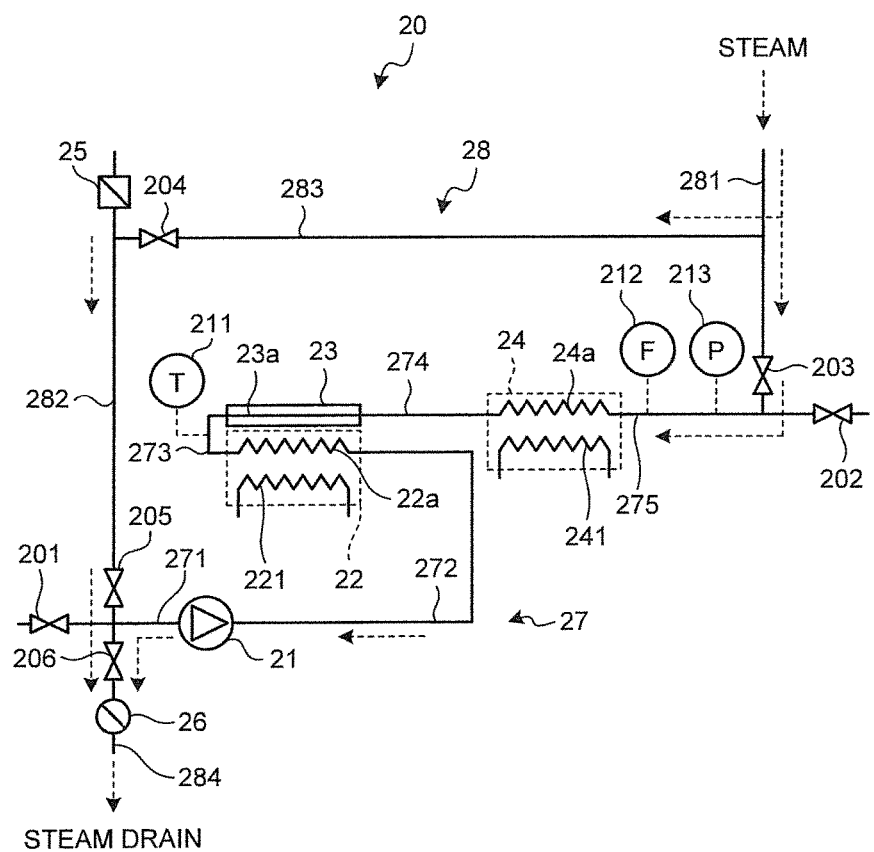
FIG. 3 is a diagram illustrating the pretreatment in the fermenting system according to the first example.
Figure 4:
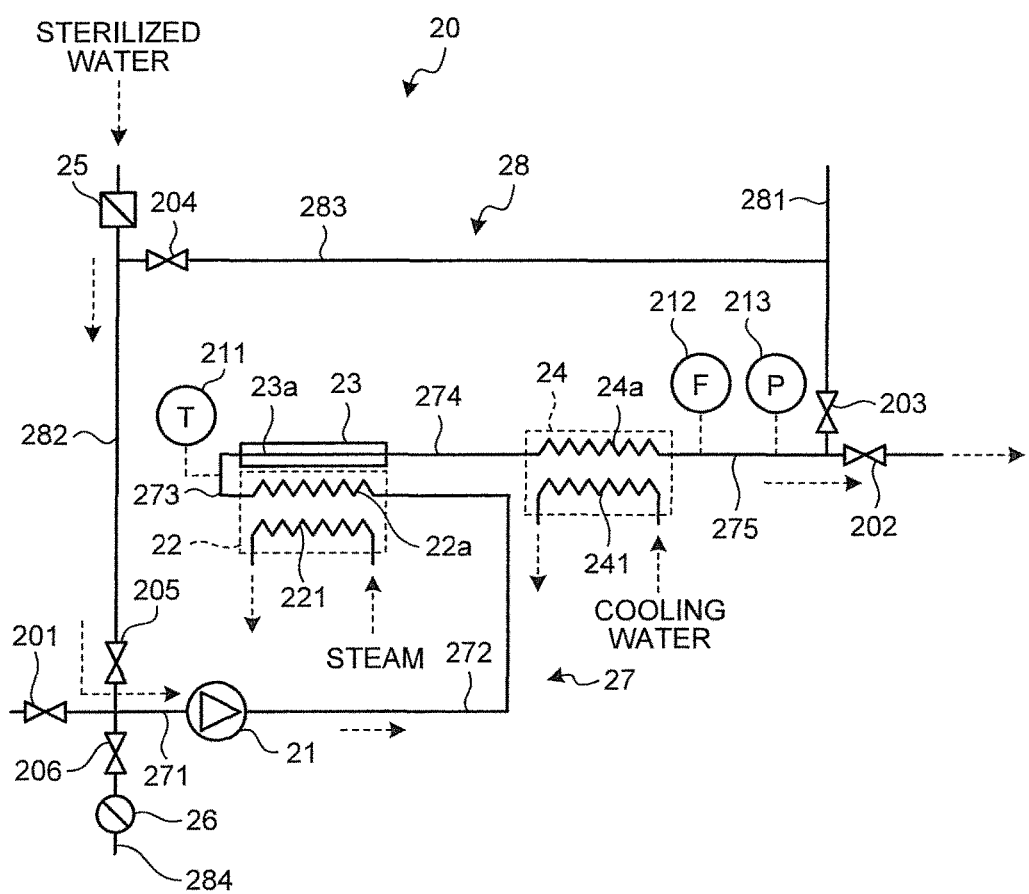
FIG. 4 is a diagram illustrating the pretreatment in the fermenting system according to the first example.
Figure 5:
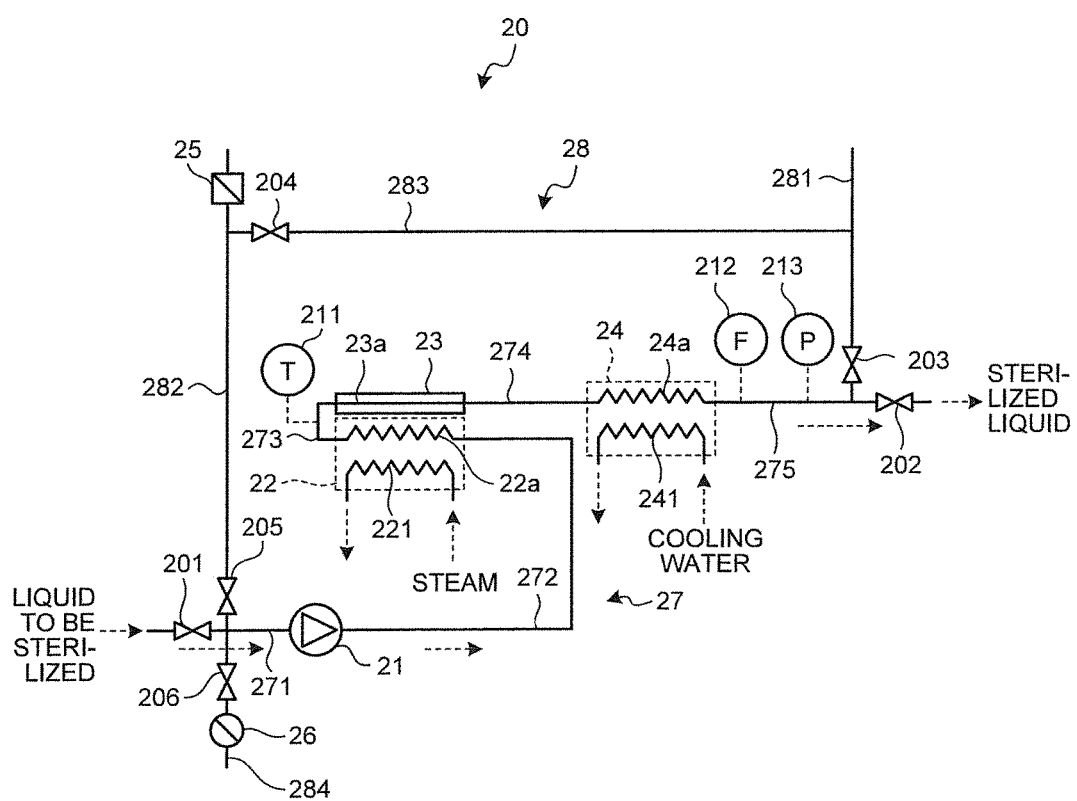
FIG. 5 is a diagram illustrating the pretreatment in the fermenting system according to the first example.

FIG. 2 is a flowchart illustrating the pretreatment in a fermenting system according to the first example. FIGS. 3 through 5 are diagrams illustrating the pretreatment in the fermenting system according to the first example. Although the following describes a case in which steam is used as the sterilizing medium, an acidic or alkaline aqueous solution may be used as the sterilizing medium. The steam may contain a boiler compound.

In the pretreatment, first, sterilization of the inside of the pipes (a member) with the steam is performed (Step S101). Steam sterilization treatment at Step S101 introduces the steam (the sterilizing medium) from the first pipe 281 and sterilizes the inside of the pipes of the continuous sterilizing apparatus 20.

During the steam sterilization treatment, the controller 40 performs control to close the first valve 201 and the second valve 202 and open the third valve 203, the fourth valve 204, the fifth valve 205, and the sixth valve 206. In other words, the first flow channel 27 and the second flow channel 28 form a nearly ring-shaped flow channel. With this configuration, the steam introduced to the first pipe 281 fills the first flow channel 27 from the fifth pipe 275, is diverted from the first pipe 281 to the third pipe 283, and is sent to the second pipe 282 to fill the second flow channel 28. In this situation, the first pipe 281, the second pipe 282, the third pipe 283, the third valve 203, the fourth valve 204, and the fifth valve 205 through which the introduced steam circulates form a second circulating unit.

The drain generated through the circulation of steam is discharged to the outside from the fourth pipe 284 via the steam trap 26 (refer to FIG. 3). The steam trap 26, the fourth pipe 284, and the sixth valve 206 form a fourth circulating unit. When sterilization of the fermenter 31 is simultaneously performed, the drain generated through steam that has flowed into the fermenter 31 may be discharged via the steam trap 32 by opening the second valve 202 and the valve 311, for example. Steam may be introduced to the fermenter from an exclusive steam supply line (not illustrated) to sterilize the fermenter.

After apparatus sterilization is sufficiently performed, introduction of the steam is stopped, and sterilized air is introduced from the first pipe 281, thereby maintaining the intra-pipe pressure of the first flow channel 27 and the second flow channel 28 at a positive pressure (Step S102). The introduction of the sterilized air prevents the inside of the pipes from becoming a negative pressure when the inside of the pipes is cooled by the stop of the introduction of the steam. This operation is technically common knowledge when performing apparatus sterilization.

Next, the second valve 202 is opened from the closed state under the control of controller 40, and the third valve 203, the fourth valve 204, and the sixth valve 206 are closed from the open state to introduce the sterilizing liquid from the second pipe 282 (refer to Step S103 and FIG. 4). As described above, the sterilizing liquid used in this example is the sterilized water adjusted to have a viscosity or the like similar to that of the actual liquid to be sterilized. The sterilizing liquid passes through the sterilizing filter 25, thereby being subjected to sterilization treatment. The second pipe 282 and the fifth valve 205 through which the introduced sterilizing liquid circulates form a third circulating unit.

When the sterilizing liquid is introduced from the second pipe 282, the sterilizing liquid flows into the first pipe 271, circulates through the first flow channel 27 toward the downstream side, and then flows into the fermenter 31. In this situation, the heating unit 22, the holding unit 23, and the cooling unit 24 operate under the control of the controller 40. The sterilizing liquid circulates through the first flow channel 27, thereby being heated by the heating unit 22 to have a certain temperature, being held by the holding unit 23 for a certain time at a certain temperature, and being cooled by the cooling unit 24. Specifically, the sterilizing liquid is, for example, heated by the heating unit 22 up to about 135° C., is held by the holding unit 23 at 135° C. for 1 minute, and cooled by the cooling unit 24 to 32° C. The sterilizing liquid fed to the fifth pipe 275 then flows into the fermenter 31.

While the sterilizing liquid is circulated through the first flow channel 27, the controller 40 acquires a temperature, a flow rate, and an intra-pipe pressure depending on the sterilizing liquid circulating through the first flow channel 27 as pieces of measurement information from the thermometer 211, the flow meter 212, and the pressure gauge 213, respectively. The controller 40 refers to the sterilization condition information 51 stored in the storage unit 50 and determines whether the temperature, the flow rate, and the intra-pipe pressure of the sterilizing liquid circulating through the pipes satisfy set sterilization conditions based on the acquired pieces of measurement information (Step S104).

Specifically, based on temperature information from the thermometer 211, the controller 40 determines whether the temperature of the liquid circulating through the third pipe 273 is a predetermined temperature. The controller 40 controls a temperature and flow rate of steam to be circulated through the pipe 221 in accordance with the determination result.

Based on information on the flow rate from the flow meter 212, the controller 40 determines whether the flow rate of the liquid circulating through the fifth pipe 275 is a predetermined flow rate. The controller 40 controls the operation of the pressure feed pump 21 in accordance with the determination result.

Based on pressure information from the pressure gauge 213, the controller 40 determines whether the intra-pipe pressure of the fifth pipe 275 is a predetermined pressure. The controller 40 adjusts the degree of opening of the second valve 202 so that the liquid within the pipes of the first flow channel 27 does not boil in accordance with the determination result to perform internal pressure control.

When the controller 40 compares the pieces of measurement information acquired from the thermometer 211, the flow meter 212, and the pressure gauge 213 with the sterilization condition information 51 and determines that the sterilization conditions are not satisfied (No at Step S104), the control of the temperature, the flow rate, and/or the pressure is performed, and the comparison processing at Step S104 is repeated.

In contrast, when the controller 40 compares the pieces of measurement information acquired from the thermometer 211, the flow meter 212, and the pressure gauge 213 with the sterilization condition information 51 and determines that the sterilization conditions are satisfied (Yes at Step S104), the process proceeds to Step S105.

When the controller 40 determines that the sterilization conditions are satisfied, the fact that the sterilization conditions have been satisfied may be informed. Such informing means can be implemented by any of sound, light, image display such as a buzzer, an LED, and monitor display or any combination thereof.

If the controller 40 determines that the sterilization conditions are satisfied, the controller 40 performs control to close the fifth valve 205 from the open state and open the first valve 201 from the closed state and switches the liquid to be supplied to the first flow channel from the sterilizing liquid to the liquid to be sterilized (Step S105). With this operation, the liquid to be sterilized such as a culture medium, a food product, and a pharmaceutical is supplied from the raw material holding unit 10 to the continuous sterilizing apparatus 20 (refer to FIG. 5).

By performing the pretreatment, the inside of the pipes can be sterilized, and the heating temperature, the holding temperature, the cooling temperature, the flow rate, and the pressure in the continuous sterilizing apparatus 20 can be stabilized before the liquid to be sterilized is circulated through the inside of the pipes of the first flow channel 27, and after that, the sterilizing liquid is switched to the liquid to be sterilized, thereby enabling the sterilization treatment on the liquid to be sterilized to be continuously performed with the predetermined circulation conditions satisfied under the sterilized environment.

After the pretreatment, the liquid to be sterilized (a culture medium or the like) sterilized by the continuous sterilizing apparatus 20 is sent to the fermenter 31, thereby enabling the fermentation treatment to be performed in the fermenting apparatus 30. In the fermenter 31, a microorganism or cultured cell prepared by a pre-culturing apparatus (not illustrated) is planted, and the fermentation treatment is performed by a supply of the culture medium from the continuous sterilizing apparatus 20. The fermenting apparatus 30 performs temperature adjustment within the fermenter 31, a supply of a gas, or the like in accordance with fermentation conditions.

In the fermentation treatment, the controller 40 appropriately acquires the pieces of measurement information from the thermometer 211, the flow meter 212, and the pressure gauge 213, refers to the sterilization condition information 51, and determines whether the temperature, the flow rate, and the intra-pipe pressure of the sterilizing liquid circulating through the pipes satisfy the set sterilization conditions based on the acquired pieces of measurement information, thereby controlling the temperature, the flow rate, and the intra-pipe pressure. As to the flow rate, apart from the acquisition of a measured value by the flow meter 212, a measured value may be acquired in accordance with a weight change in the raw material holding unit 10 or a weight change in the fermenter 31, and alternatively, a measured value may be acquired through a combination thereof.

The first example performs sterilization with the sterilizing medium and adjusts the sterilization conditions with the sterilizing liquid via the second flow channel 28 connected to the upstream side and the downstream side of the first flow channel 27 that circulates the liquid to be sterilized, thereby eliminating a cooling unit that has been required in the second flow channel, surely performing the sterilization treatment within the flow channel, and achieving downsizing of the apparatus.

The first example can achieve shift from the sterilization treatment on the pipes to the sterilization treatment on the liquid to be sterilized without impairing sterilizability through the sterilization with the steam and the adjustment of the sterilization conditions using the sterilized water as the pretreatment.

Although it is described in the first example that the valves provided in the pipes are operated to open and close under the control of the controller 40, the opening and closing of the valves described above may be manually performed by a user.

Second Example

Figure 6:
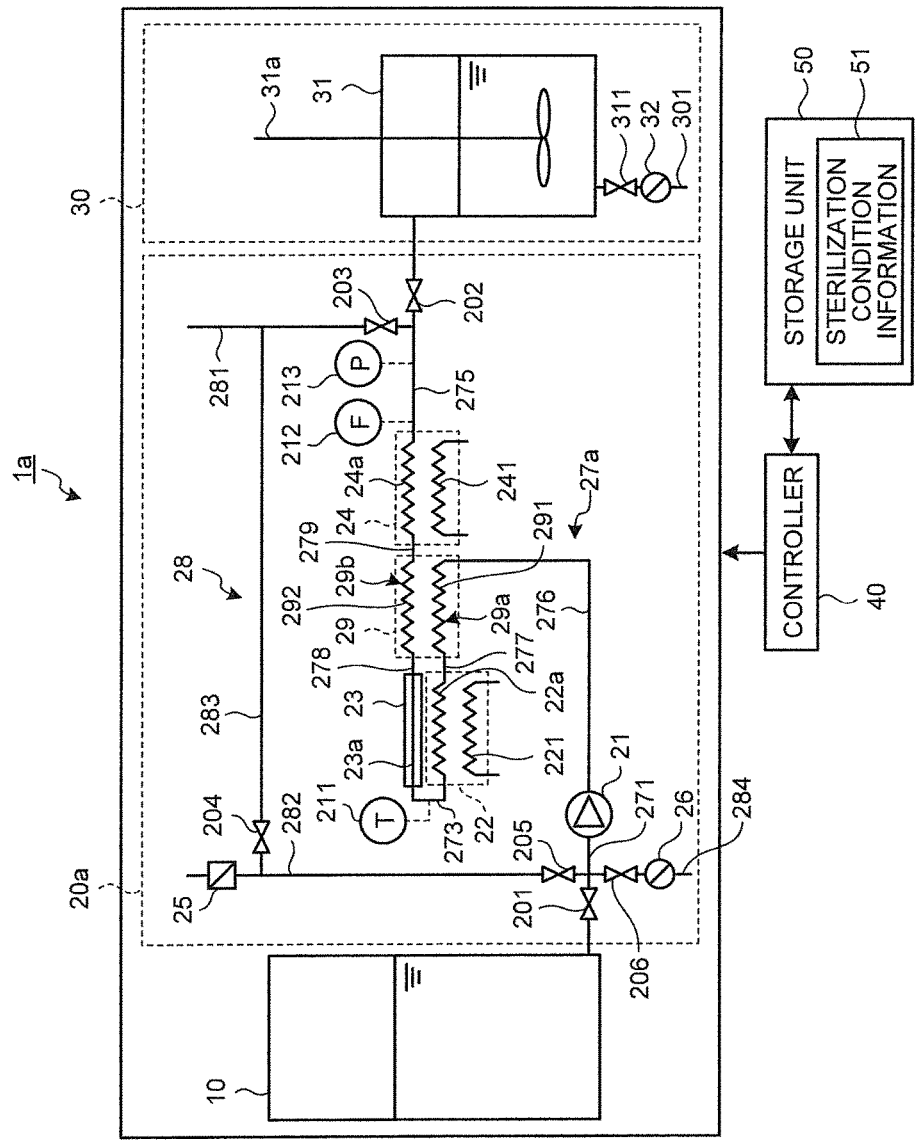
FIG. 6 is a schematic diagram illustrating a rough configuration of a fermenting system according to a second example.
Figure 7:
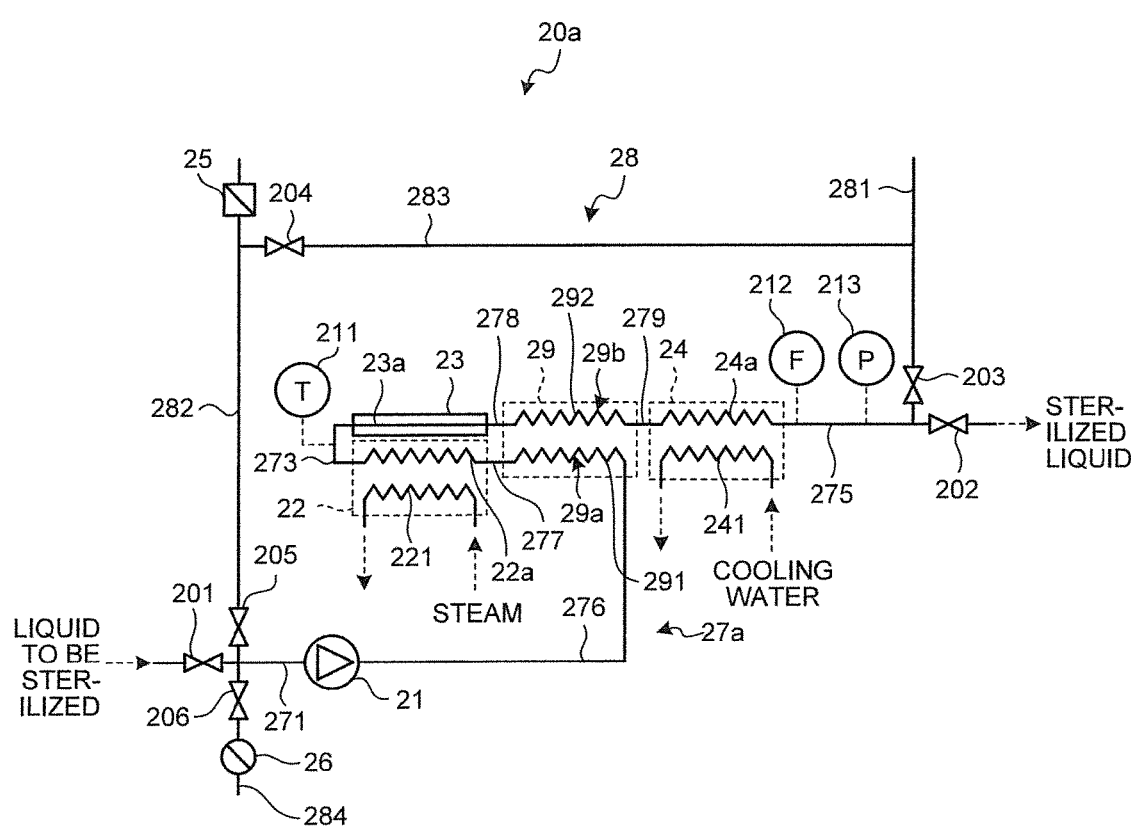
FIG. 7 is a schematic diagram illustrating a rough configuration of a continuous sterilizing apparatus in the fermenting system according to the second example.

FIG. 6 is a schematic diagram illustrating a rough configuration of a fermenting system according to a second example. FIG. 7 is a schematic diagram illustrating a rough configuration of a continuous sterilizing apparatus according to the second example. The same components as the components of the first example are attached with the same symbols. As illustrated in FIG. 6, this fermenting system 1a according to the second example includes a continuous sterilizing apparatus 20a in place of the continuous sterilizing apparatus 20 of the fermenting system 1. The continuous sterilizing apparatus 20a includes, in addition to the components of the continuous sterilizing apparatus 20 according to the first example, a heat exchange unit 29 that causes the liquid before and after the heating treatment by the heating unit 22 and the holding unit 23 to perform heat exchange in an auxiliary manner.

In the sterilizing apparatus 20a, the pressure feed pump 21, the heating unit 22, the holding unit 23, the cooling unit 24, and the heat exchange unit 29 are connected with pipes to form a first flow channel 27a as a flow channel. The sterilizing apparatus 20a forms the second flow channel 28 respective both ends of which are connected to the upstream side and the downstream side of the first flow channel 27a.

The heat exchange unit 29 includes a first heat exchange unit 29a provided at the front (upstream side) of the heating unit 22 in the first flow channel 27a and a second heat exchange unit 29b provided at the rear (downstream side) of the holding unit 23 in the first flow channel 27a.

The first flow channel 27a includes the first pipe 271, the third pipe 273, the fifth pipe 275, a sixth pipe 276 that connects between the pressure feed pump 21 and the heat exchange unit 29 (the first heat exchange unit 29a), a seventh pipe 277 that connects between the heat exchange unit 29 (the first heat exchange unit 29a) and the upstream side of the heating unit 22, an eighth pipe 278 that connects between the downstream side of the holding unit 23 and the heat exchange unit 29 (the second heat exchange unit 29b), and a ninth pipe 279 that connects between the heat exchange unit 29 (the second heat exchange unit 29b) and the cooling unit 24.

The first heat exchange unit 29a includes a pipe 291 one end of which connects to the sixth pipe 276 and the other end of which connects to the seventh pipe 277. The second heat exchange unit 29b includes a pipe 292 one end of which connects to the eighth pipe 278 and the other end of which connects to the ninth pipe 279. The heat exchange unit 29 is arranged so that the pipe 291 and the pipe 292 are close to each other or that the outer surfaces of the pipe 291 and the pipe 292 are in contact with each other. With this configuration, the heat exchange unit 29 performs heat exchange via the pipe 291 and the pipe 292 between a nearly room temperature liquid sent from the raw material holding unit 10 or the second pipe 282 via the sixth pipe 276 and a liquid having passed through the holding unit 23 to be maintained at a certain temperature (135° C., for example). The heat exchange unit 29 may include a plate type heat exchanger formed by separating the first heat exchange unit 29a and the second heat exchange unit 29b from each other with a heat exchanger wall.

Heat exchange is performed between the liquids by the heat exchange unit 29, thereby causing the liquid to be sterilized having a temperature higher than the temperature of the liquid to be sterilized supplied from the raw material holding unit 10 to be fed to the pipe 22a of the heating unit 22 and causing the liquid to be sterilized having a temperature lower than the temperature of the liquid to be sterilized supplied from the holding unit 23 to be fed to the pipe 24a of the cooling unit 24. With this operation, adjustment ranges of temperature adjustment separately performed by the heating unit 22 and the cooling unit 24 can be reduced, and thermal energy can be collected. Similar heat exchange is performed also in the circulation of the sterilizing liquid in the pretreatment.

The second example, similarly to the first example, performs sterilization with the steam and adjusts the sterilization conditions with the sterilized water via the second flow channel 28 connected to the upstream side and the downstream side of the first flow channel 27a that circulates the liquid to be sterilized, thereby eliminating a cooling unit that has been required in the second flow channel 28, surely performing the sterilization treatment within the flow channel, and achieving downsizing of the apparatus.

Figure 10:
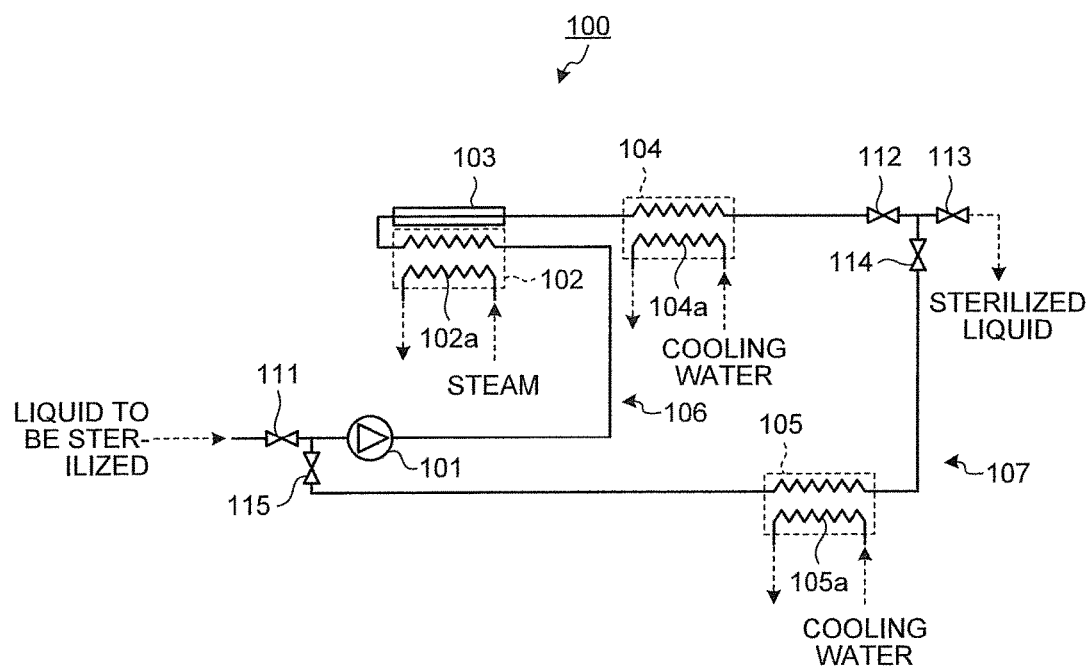
FIG. 10 is a schematic diagram illustrating an example of a rough configuration of a conventional multi-pipe type continuous sterilizing apparatus.

When a heat exchange unit is provided in the conventional continuous sterilizing apparatus 100 as illustrated in FIG. 10, the continuous sterilizing apparatus 100 circulates a liquid (a liquid having a viscosity or the like similar to that of the actual liquid to be sterilized) heated by the heating unit 102, thereby performing sterilization, but the heated liquid sent from the holding unit 103 is cooled by the heat exchange unit. In this situation, a liquid the temperature of which is lower than the temperature of the liquid heated by the heating unit circulates through the pipe following the cooling unit 104 connected to the downstream side of the heat exchange unit, and sterilization may be insufficient.

When the sterilization of the continuous sterilizing apparatus 100 is not sufficient, even when the liquid to be sterilized is heated by a heater to a certain high temperature and certain sterilization treatment is performed, being in contact with a section (following the cooling unit 104) in which the sterilization of the continuous sterilizing apparatus 100 is insufficient causes a problem of contamination of the liquid to be sterilized with various bacteria or the like. When a culture medium is continuously supplied in a continuous fermenting process in the fermenting industry in particular, minute faulty sterilization of the continuous sterilizing apparatus 100 causes contamination with various bacteria and leads to a signification problem such as inability to perform continuous fermentation treatment for a long time.

In contrast, the second example provides the heat exchange unit 29 that performs heat exchange on the circulating liquid before and after the heating treatment by the heating unit 22 and the holding unit 23, thereby achieving heating and cooling on the liquid by performing thermal energy collection more efficiently. The steam is circulated from the downstream side of the first flow channel 27a toward the upstream side thereof via the second flow channel 28 to perform sterilization treatment, and sure sterilization treatment can be performed.

The second example can achieve shift from the sterilization treatment on the pipes to the sterilization treatment on the liquid to be sterilized without impairing sterilizability through the sterilization with the steam and the adjustment of the sterilization conditions using the sterilized water as the pretreatment.

Third Example

Figure 8:
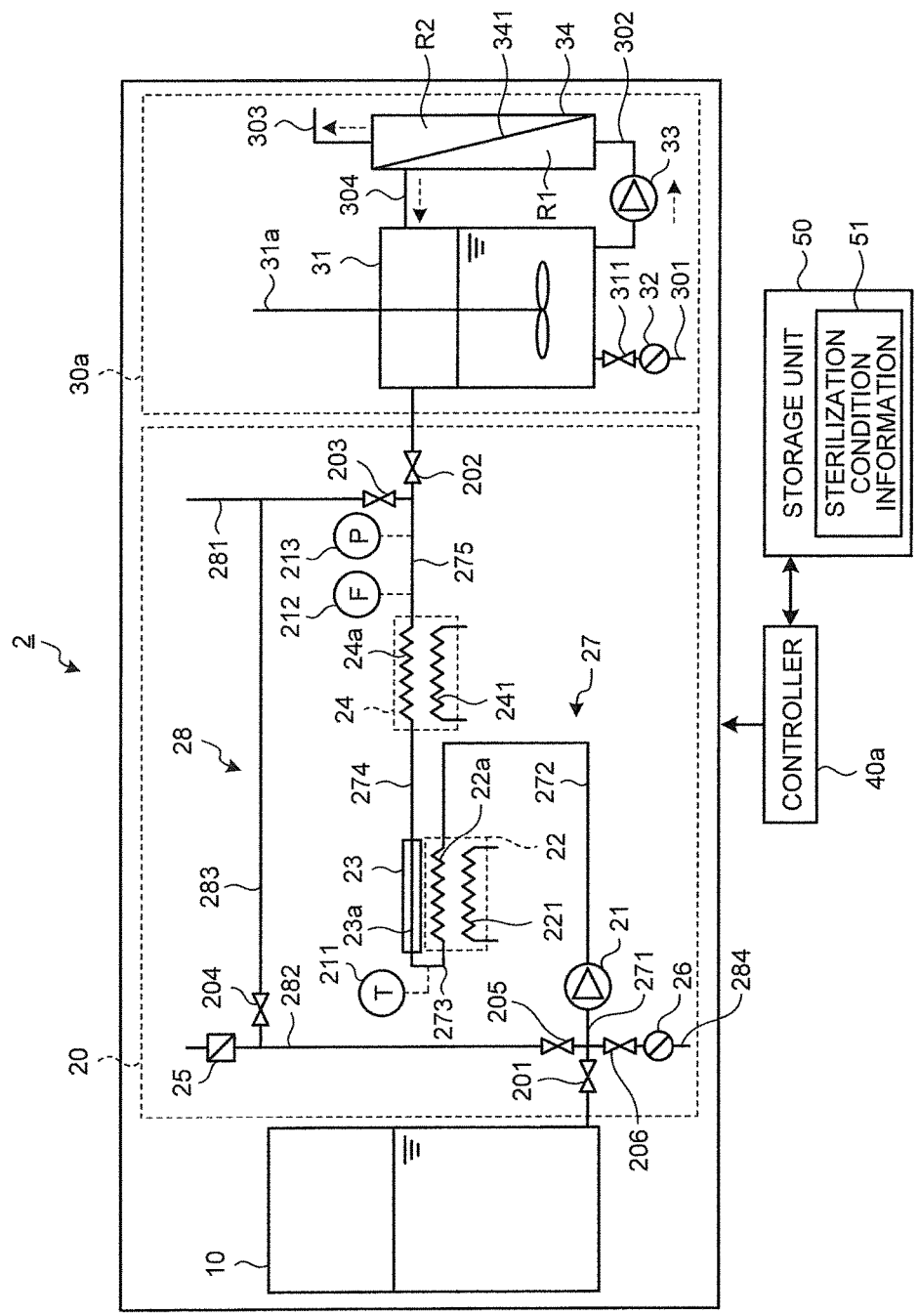
FIG. 8 is a schematic diagram illustrating a rough configuration of a continuous sterilizing apparatus according to a third example.

FIG. 8 is a schematic diagram illustrating a rough configuration of a continuous fermenting system according to a third example. This continuous fermenting system 2 according to the third example houses a microorganism for culture or cultured cell, continuously supplies a culture medium to a fermenter that generates a fermented liquid by fermentation, separates the fermented liquid from the microorganism and cultured cell discharged from the fermenter with a separation membrane, and performs circulation that returns an unfiltrated liquid (containing the microorganism or cultured cell) to the fermenter, thereby collecting the fermented liquid continuously for a long time while maintaining high productivity.

The continuous fermenting system 2 illustrated in FIG. 8 includes the raw material holding unit 10, the continuous sterilizing apparatus 20 and the storage unit 50, a fermenting apparatus 30a that performs fermentation treatment using a raw material subjected to sterilization treatment by the continuous sterilizing apparatus 20, and a controller 40a that includes a central processing unit (CPU) and controls the entire operation of the continuous fermenting system 2. The storage unit 50 stores therein various kinds of programs for operating the continuous fermenting system 2 and information containing various kinds of parameters required for operation of the continuous fermenting system 2.

The fermenting apparatus 30a includes the fermenter 31 coupled to the continuous sterilizing apparatus 20 and houses and ferments a culture medium, a food product, or a pharmaceutical sterilized by the continuous sterilizing apparatus 20 and a microorganism, a cultured cell, or the like, the steam trap 32 that discharges only drain within a steam atmosphere, a pressure feed pump 33 that pressure feeds the fermented liquid from the fermenter 31, and a separation membrane module 34 (a filtration unit) that filtrates the fermented liquid fed by the pressure feed pump 33.

The fermenting apparatus 30a includes a first pipe 301 one end of which connects to the fermenter 31 and includes the steam trap, a second pipe 302 one end of which connects to the fermenter 31, the other end of which connects to the separation membrane module 34, and includes the pressure feed pump 33, a third pipe 303 one end of which connects to the separation membrane module 34, and a fourth pipe 304 one end of which connects to the separation membrane module 34 and the other of which connects to the fermenter 31.

The second pipe 302 forms a flow channel that sends the sterilized culture medium, food product, or pharmaceutical, the fermented liquid obtained by fermenting them with the microorganism or cultured cell, or the like from the fermenter 31 to the separation membrane module 34 via the pressure feed pump 33.

The separation membrane module 34 is nearly box-shaped and contains therein a porous film 341 in which a plurality of pores the average diameter of which is, for example, 0.01 μm or more and less than 1.00 μm are formed. The porous film 341 is, for example, provided to form two areas R1 and R2 by dividing the internal space of the separation membrane module 34. In other words, the internal space of the separation membrane module 34 is divided by the porous film 341, and the equally divided spaces communicate with each other only through the pores.

The porous film 341 is formed of an organic film formed of an organic material and/or an inorganic film formed of an inorganic material or the like. Preferable examples of the organic film include organic films containing organic polymer compounds exemplified by polyethylene-based resins, polypropylene-based resins, polyvinyl chloride-based resins, poly(vinylidene fluoride)-based resins, polysulfone-based resins, polyether sulfone-based resins, polyacrylonitrile-based resins, cellulose-based resins, and cellulose triacetate-based resins. Among them, preferable are polyvinyl chloride-based resins, poly(vinylidene fluoride)-based resins, polysulfone-based resins, polyether sulfone-based resins, and polyacrylonitrile-based resins, which can easily form films through solutions and are excellent in physical durability and chemical resistance. Poly(vinylidene fluoride)-based resins or resins having the resins as the main component are most preferable. The inorganic film is preferably formed of ceramic materials.

In the separation membrane module 34, the second pipe 302 and the fourth pipe 304 are connected to communicate with the area R1, whereas the third pipe 303 is connected to communicate with the area R2.

The separation membrane module 34 filtrates the fermented liquid fed from the fermenter 31 by the porous film 341. Specifically, the fermented liquid having passed through the pores of the porous film 341 is introduced to the area R2 and sent to the outside via the third pipe 303. The fermented liquid (an unfiltrated liquid such as a substance larger than the diameter of the pores such as a microorganism and a cultured cell) that has not been able to pass through the pores of the porous film 341 remains in the area R1 and returns to the fermenter 31 via the fourth pipe 304.

In the separation membrane module 34, the internal space may be divided by the porous film 341, or a hollow fiber separation membrane module including a plurality of hollow fiber membranes may be used. When the hollow fiber separation membrane module is used, in an external pressure type hollow fiber separation membrane module, for example, the second pipe 302 and the fourth pipe 304 are connected to communicate with a space (corresponding to the area R1) formed by the outer surfaces of the hollow fiber membranes, whereas the third pipe 303 is connected to communicate with a space (corresponding to the area R2) formed by the inner surfaces of the hollow fiber membranes. In an internal pressure type hollow fiber separation membrane module, the second pipe 302 and the fourth pipe 304 are connected to communicate with the space formed by the inner surfaces of the hollow fiber membranes, whereas the third pipe 303 is connected to communicate with the space formed by the outer surfaces of the hollow fiber membranes.

In the continuous fermenting system 2, the raw material subjected to the sterilization treatment by the continuous sterilizing apparatus 20 described above is supplied to the fermenter 31. Specifically, the raw material supplied from the raw material holding unit 10 is subjected to the heating sterilization treatment by the continuous sterilizing apparatus 20 and fed to the fermenter 31 via the fifth pipe 275. In the fermenter 31, fermentation treatment is performed on the raw material fed from the continuous sterilizing apparatus 20 and the microorganism or cultured cell, and the fermented liquid generated by the fermentation treatment is sent to the separation membrane module 34. The liquid filtrated by the separation membrane module 34 is collected via the third pipe 303, whereas the fermented liquid (the unfiltrated liquid) remaining through filtration containing the microorganism or cultured cell returns to the fermenter 31 via the fourth pipe 304. By performing the series of pieces of treatment, the fermentation treatment is continuously performed, and the fermented liquid can be collected. In the series of pieces of treatment, the controller 40a performs control to open only the first valve 201 and the second valve 202 and close the third valve 203 through the sixth valve 206 and the valve 311.

In the fermenter 31, a microorganism or cultured cell prepared by a pre-culturing apparatus (not illustrated) is planted, and continuous fermentation treatment is performed by repeatedly performing a supply of the culture medium from the continuous sterilizing apparatus 20 and the filtration (a resupply of the microorganism or cultured cell within the separation membrane module 34 to the fermenter 31 and collection of the fermented liquid from which the microorganism or cultured cell has been separated and removed) by the separation membrane module 34. The fermenting apparatus 30a performs temperature adjustment within the fermenter 31, a supply of a gas, or the like in accordance with fermentation conditions.

The third example, similarly to the first example, performs sterilization with the sterilizing medium and adjusts the sterilization conditions with the sterilizing liquid via the second flow channel 28 connected to the upstream side and the downstream side of the first flow channel 27 that circulates the liquid to be sterilized, thereby eliminating a cooling unit that has been required in the second flow channel, surely performing the sterilization treatment within the flow channel, and achieving downsizing of the apparatus.

The third example can achieve shift from the sterilization treatment on the pipes to the sterilization treatment on the liquid to be sterilized without impairing sterilizability through the sterilization with the steam and adjustment of the sterilization conditions using the sterilized water as the pretreatment.

The third example can perform fermentation treatment continuously with sterilizability maintained by providing the separation membrane module 34 in the fermenting apparatus 30a.

Modification of the Third Example

Figure 9:
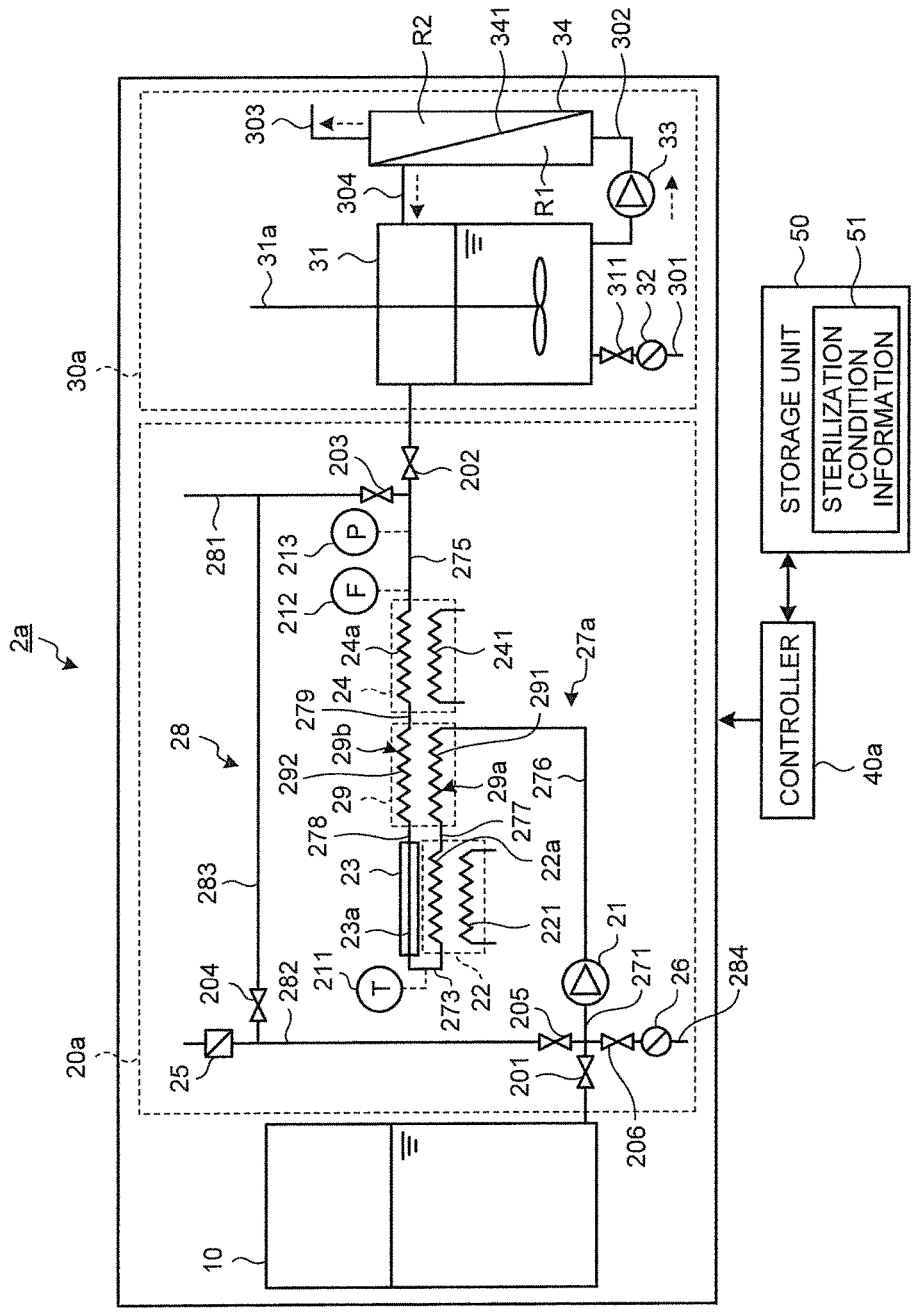
FIG. 9 is a schematic diagram illustrating a rough configuration of a continuous sterilizing system according to a modification of the third example.

FIG. 9 is a schematic diagram illustrating a rough configuration of a continuous fermenting system according to a modification of the third example. As illustrated in FIG. 9, this continuous fermenting system 2a according to the modification of the third example includes a continuous sterilizing apparatus 20a including the heat exchange unit 29 in place of the continuous sterilizing apparatus 20 of the continuous fermenting system 2. With this configuration, also in the continuous fermenting system 2a that continuously performs fermentation treatment, adjustment ranges of temperature adjustment separately performed by the heating unit 22 and the cooling unit 24 can be reduced, and thermal energy can be collected.

By providing the separation membrane module 34 in the fermenting apparatus 30a and providing the heat exchange unit 29 in the continuous sterilizing apparatus 20a as in the modification of the third example, thereby performing heating and cooling on the liquid by performing more efficient thermal energy collection in the sterilization treatment and performing fermentation treatment continuously with sterilizability maintained.

Although it is described in the first to third example and the modification that one raw material holding unit 10 is included, two or more raw material holding units 10 may be included or included in a replaceable manner. In this case, the respective raw material holding units connect to the first pipe 271, and respective valves are provided that control circulation to the first pipe 271.

In the first to third example and the modification, the second pipe 282 as the flow channel to introduce the sterilizing liquid may be diverted from a pipe (not illustrated) as a flow channel to introduce a liquid such as sterilized water to the fermenter 31. Also in this case, the liquid having passed through the sterilizing filter 25 preferably circulates through the second pipe 282 and the fermenter 31.

Although it is described in the first to third example and the modification that the pipe to introduce the sterilizing medium is the first pipe 281 and connects to the downstream side of the first flow channels 27 and 27a and the second pipe 282, the third pipe 283 may not be included, if the second pipe 282 can independently maintain its sterilized state. In other words, as an applicable configuration, the sterilizing medium may be introduced only to the downstream side of the first flow channels 27 and 27a via the first pipe 281. In this case, the first pipe 281 and the third valve 203 constitute the second circulating unit.

INDUSTRIAL APPLICABILITY

The method of operating a continuous sterilizing apparatus, the continuous sterilizing apparatus, the fermenting system, and the continuous fermenting system can suitably be employed to perform sterilization treatment on the inside of the pipes and downsizing the apparatus. In other words, we provide a continuous sterilizing apparatus that can perform heat recovery without impairing the sterilizability of the continuous sterilizing apparatus and can be extremely useful in various fields such as medical treatment, pharmaceuticals manufacture, pharmaceuticals development, biological research, food products manufacture, and organic compounds manufacture in addition to fermentation-related fields.

The invention claimed is:

1. A continuous sterilizing apparatus that sterilizes a liquid to be sterilized, the continuous sterilizing apparatus comprising:
a first circulating unit comprising:
  a heating unit configured to heat the liquid to be sterilized;
  a holding unit configured to hold the liquid to be sterilized heated by the heating unit at a certain temperature for a certain time; and
  a cooling unit configured to cool the liquid to be sterilized held by the holding unit and for which heating sterilization has been completed,
  wherein the first circulating unit circulates at least the liquid to be sterilized;
a second circulating unit including:
a first pipe, one end of which introduces a sterilizing medium that sterilizes members by which a first flow channel is formed and another end of which is connected to a downstream side of the first circulating unit;
a second pipe, one end of which introduces a sterilizing liquid subjected to one or more sterilization treatments and another end of which is connected to an upstream side of the first circulating unit; and
a third pipe, one end of which is connected to the first pipe and another end of which is connected to the second pipe, the second circulating unit forming a ring-shaped second flow channel along with the first circulating unit;

a measuring unit that measures a flow rate, a temperature, and a pressure of a liquid circulating through the first circulating unit;

a storage unit that stores a flow rate, a temperature, and a pressure related to one or more sterilization treatments on the liquid to be sterilized as condition information; and a controller that controls entire operation of the continuous sterilizing apparatus, the controller configured to:

control the second circulating unit so as to circulate the sterilizing medium through the first and the second circulating units to sterilize the first and the second circulating units and then circulate the sterilizing liquid through the first circulating unit;

perform a series of pieces of treatment by the heating unit, the holding unit, and the cooling unit on the sterilizing liquid and cause the measuring unit to measure a flow rate, a temperature, and a pressure of the sterilizing liquid subjected to the series of pieces of treatment, and compare the flow rate, the temperature, and the pressure measured by the measuring unit to the condition information stored in the storage unit, determine whether the measured flow rate, temperature, and pressure satisfy conditions corresponding to the condition information, and control the first and the second circulating units, when it is determined that the conditions are satisfied, to switch a liquid to be circulated through the first circulating unit from the sterilizing liquid to the liquid to be sterilized.

2. The continuous sterilizing apparatus according to claim 1, wherein the sterilizing medium is steam, and the continuous sterilizing apparatus further comprises a fourth circulating unit connected to the first circulating unit, the fourth circulating unit being configured to drain discharge generated by the steam.

3. The continuous sterilizing apparatus according to claim 1, further comprising a heat exchange unit that causes heat exchange between respective liquids that circulate through an upstream side of the heating unit and a downstream side of the holding unit.

4. The continuous sterilizing apparatus according to claim 3, wherein at least one of the heating unit, the cooling unit, and the heat exchange unit is a plate-type heat exchanger.

5. A fermenting system comprising:

a raw material holding unit that holds a raw material such as a culture medium, a food product, and a pharmaceutical;

a continuous sterilizing apparatus continuously sterilizing the raw material supplied from the raw material holding unit as the liquid to be sterilized, the continuous sterilizing apparatus comprising:

a first circulating unit comprising:

a heating unit that heats the liquid to be sterilized;

a holding unit that holds the liquid to be sterilized heated by the heating unit at a certain temperature for a certain time; and a cooling unit that cools the liquid to be sterilized held by the holding unit and for which heating sterilization has been completed, wherein the first circulating unit circulates at least the liquid to be sterilized;

a second circulating unit including:

a first pipe, one end of which introduces a sterilizing medium that sterilizes members by which a first flow channel is formed and another end of which is connected to a downstream side of the first circulating unit;

a second pipe, one end of which introduces a sterilizing liquid subjected to one or more sterilization treatments and another end of which is connected to an upstream side of the first circulating unit; and a third pipe, one end of which is connected to the first pipe and another end of which is connected to the second pipe, the second circulating unit forming a ring-shaped second flow channel along with the first circulating unit;

a measuring unit measures a flow rate, a temperature, and a pressure of a liquid circulating through the first circulating unit;

a storage unit stores a flow rate, a temperature, and a pressure related to one or more sterilization treatments on the liquid to be sterilized as condition information; and a controller controls entire operation of the continuous sterilizing apparatus, the controller being configured to:

control the second circulating unit so as to circulate the sterilizing medium through the first and the second circulating units to sterilize the first and the second circulating units and then circulate the sterilizing liquid through the first circulating unit;

perform a series of pieces of treatment by the heating unit, the holding unit, and the cooling unit on the sterilizing liquid and cause the measuring unit to measure a flow rate, a temperature, and a pressure of the sterilizing liquid subjected to the series of pieces of treatment, and compare the flow rate, the temperature, and the pressure measured by the measuring unit with the condition information stored in the storage unit, determine whether the measured flow rate, temperature, and pressure satisfy conditions corresponding to the condition information, and control the first and the second circulating units, when it is determined that the conditions are satisfied, to switch a liquid to be circulated through the first circulating unit from the sterilizing liquid to the liquid to be sterilized; and a fermenter that performs fermentation treatment using the raw material subjected to sterilization treatment by the continuous sterilizing apparatus.

6. The fermenting system according to claim 5, wherein the flow rate is determined in accordance with a measurement result by the measuring unit, a weight change of the raw material holding unit, and/or a weight change of the fermenter.

7. The fermenting system according to claim 5, wherein the sterilizing liquid is introduced to the flow channel via a pipe diverted from a pipe that introduces the sterilizing liquid to the fermenter.

8. A continuous fermenting system comprising:

a fermenting system comprising:

a raw material holding unit that holds a raw material such as a culture medium, a food product, and a pharmaceutical;

a continuous sterilizing apparatus continuously sterilizing the raw material supplied from the raw material holding unit as the liquid to be sterilized, the continuous sterilizing apparatus comprising:

a first circulating unit comprising:

a heating unit that heats the liquid to be sterilized;

a holding unit that holds the liquid to be sterilized heated by the heating unit at a certain temperature for a certain time; and a cooling unit that cools the liquid to be sterilized held by the holding unit and for which heating sterilization has been completed, wherein the first circulating unit circulates at least the liquid to be sterilized;

a second circulating unit including:

a first pipe, one end of which introduces a sterilizing medium that sterilizes members by which a first flow channel is formed and another end of which is connected to a downstream side of the first circulating unit;

a second pipe, one end of which introduces a sterilizing liquid subjected to one or more sterilization treatments and another end of which is connected to an upstream side of the first circulating unit; and a third pipe, one end of which is connected to the first pipe and another end of which is connected to the second pipe, the second circulating unit forming a ring-shaped second flow channel along with the first circulating unit;

a measuring unit measures a flow rate, a temperature, and a pressure of a liquid circulating through the first circulating unit;

a storage unit stores a flow rate, a temperature, and a pressure related to one or more sterilization treatments on the liquid to be sterilized as condition information; and a controller controls entire operation of the continuous sterilizing apparatus, the controller configured to:

control the second circulating unit so as to circulate the sterilizing medium through the first and the second circulating units to sterilize the first and the second circulating units and then circulate the sterilizing liquid through the first circulating unit;

perform a series of pieces of treatment by the heating unit, the holding unit, and the cooling unit on the sterilizing liquid and cause the measuring unit to measure a flow rate, a temperature, and a pressure of the sterilizing liquid subjected to the series of pieces of treatment, and compare the flow rate, the temperature, and the pressure measured by the measuring unit to the condition information stored in the storage unit, determine whether the measured flow rate, temperature, and pressure satisfy conditions corresponding to the condition information, and control the first and the second circulating units, when it is determined that the conditions are satisfied, to switch a liquid to be circulated through the first circulating unit from the sterilizing liquid to the liquid to be sterilized; and a fermenter that performs fermentation treatment using the raw material subjected to sterilization treatment by the continuous sterilizing apparatus; and a filtration unit that filters fermented liquid generated in the fermenter.

9. The continuous fermenting system according to claim 8, wherein the raw material holding unit comprises a plurality of raw material holding units.

* * * * *